United States Patent
Flohr et al.

[11] Patent Number: 5,815,546
[45] Date of Patent: Sep. 29, 1998

[54] COMPUTED TOMOGRAPHY APPARATUS FOR CONDUCTING SPIRAL SCAN WITH THE X-RAY DETECTOR TILTED RELATIVE TO THE SYSTEM AXIS

[75] Inventors: Thomas Flohr, Uehlfeld; Klaus Klingenbeck-Regn, Nuernberg; Stefan Schaller, Erlangen, all of Germany; Kwok Tam, Edison, N.J.

[73] Assignee: Siemens Aktiengesellschaft, Munich, Germany

[21] Appl. No.: 881,331

[22] Filed: Jun. 24, 1997

[30] Foreign Application Priority Data

Jun. 28, 1996 [DE] Germany .......................... 196 26 095.7

[51] Int. Cl.[6] .................................................. G01N 23/00
[52] U.S. Cl. .................................................. 378/19; 378/4
[58] Field of Search ............................................. 378/19, 4

[56] References Cited

U.S. PATENT DOCUMENTS 5,291,402  3/1994  Pfoh .
5,390,112  2/1995  Tam .
5,469,486  11/1995  Hu et al. .

FOREIGN PATENT DOCUMENTS

OS 40 15 180  11/1991  Germany .

*Primary Examiner*—Craig E. Church
*Attorney, Agent, or Firm*—Hill & Simpson

[57] ABSTRACT

A computed tomography apparatus has a surface X-ray detector composed of detection elements, with all detectors being usable in a spiral scan wherein the detector and an X-ray radiator are rotated around a system axis. The detector has a symmetry axis tilted relative to the system axis by a non-zero acute angle, this angle can be adjustable, including being settable to a value of zero for conducting a conventional spiral scan.

3 Claims, 2 Drawing Sheets

COMPUTED TOMOGRAPHY APPARATUS FOR CONDUCTING SPIRAL SCAN WITH THE X-RAY DETECTOR TILTED RELATIVE TO THE SYSTEM AXIS

BACKGROUND OF THE INVENTION

1. Field of the Invention

The present invention is directed to a computed tomography apparatus, and in particular to a computed tomography apparatus having an x-ray radiator which emits a pyramidal X-ray beam that strikes a surface detector, with the X-ray radiator and the detector being rotated, while producing relative longitudinal movement with respect to an examination subject, for conducting a spiral scan of the subject.

2. Description of the Prior Art

A computed tomography apparatus is known wherein the X-ray radiator emits a pyramidal X-ray beam that strikes a surface detector. The surface detector is thereby composed of a number of parallel detector lines, and each detector line is formed of a number of detector elements. In this way, it becomes possible to simultaneously transirradiate a number of slices during the rotation of the measurement system composed of the X-ray radiator and the detector, and thus to obtain short exposure times.

A computed tomography apparatus is also known that emits a fan-shaped X-ray beam that strikes a line-shaped detector that is composed of a number of detector elements. A spiral scan of the volume of the examination subject is achieved by a continuous rotation of the measurement system, composed of the X-ray radiator and the detector, by an angle that is greater than 360°.

A spiral scan, is likewise fundamentally possible given a computed tomography apparatus with a surface detector. A shorter scan time is thereby achieved compared to a detector that is composed of only one line. Projections from focus positions that lie opposite one another must thereby follow one another gap-free in the direction of the system axis. Overlaps thereby occur between different projections. The surface detector that is available is therefore not optimally utilized. The detector length in the direction of the system axis (z-direction) corresponds to the slope of the scan spiral. The lines of the detector lying at the edges thereby lie parallel to one another, and their data are not completely used for the image reconstruction due to the spiral scan.

SUMMARY OF THE INVENTION

An object of the present invention is to a computed tomography apparatus with a pyramidal X-ray beam and a surface detector as well as means for conducting a spiral scan of an examination subject wherein given a simple structure of the detector, a full utilization of all detector data for the image reconstruction is enabled.

The above object is achieved in accordance with the principles of the present invention in a computed tomography apparatus having an X-ray radiator and a surface detector which are rotatable around an examination subject as a measurement unit, with relative longitudinal motion between the examination unit and the subject, for conducting a spiral scan of the subject, wherein the surface detector is mounted so as to be tiltable relative to the rotational axis, so that the surface detector can be oriented at a non-zero acute angle relative to the rotational axis.

Using the subject matter of the present invention, a fast spiral scan of a volume of the examination subject can ensue with a surface detector which is rectangular in plan view and which is curved on a cylinder surface, the entire detector area is utilized in every projection.

DESCRIPTION OF THE PREFERRED EMBODIMENTS

Figure 1:
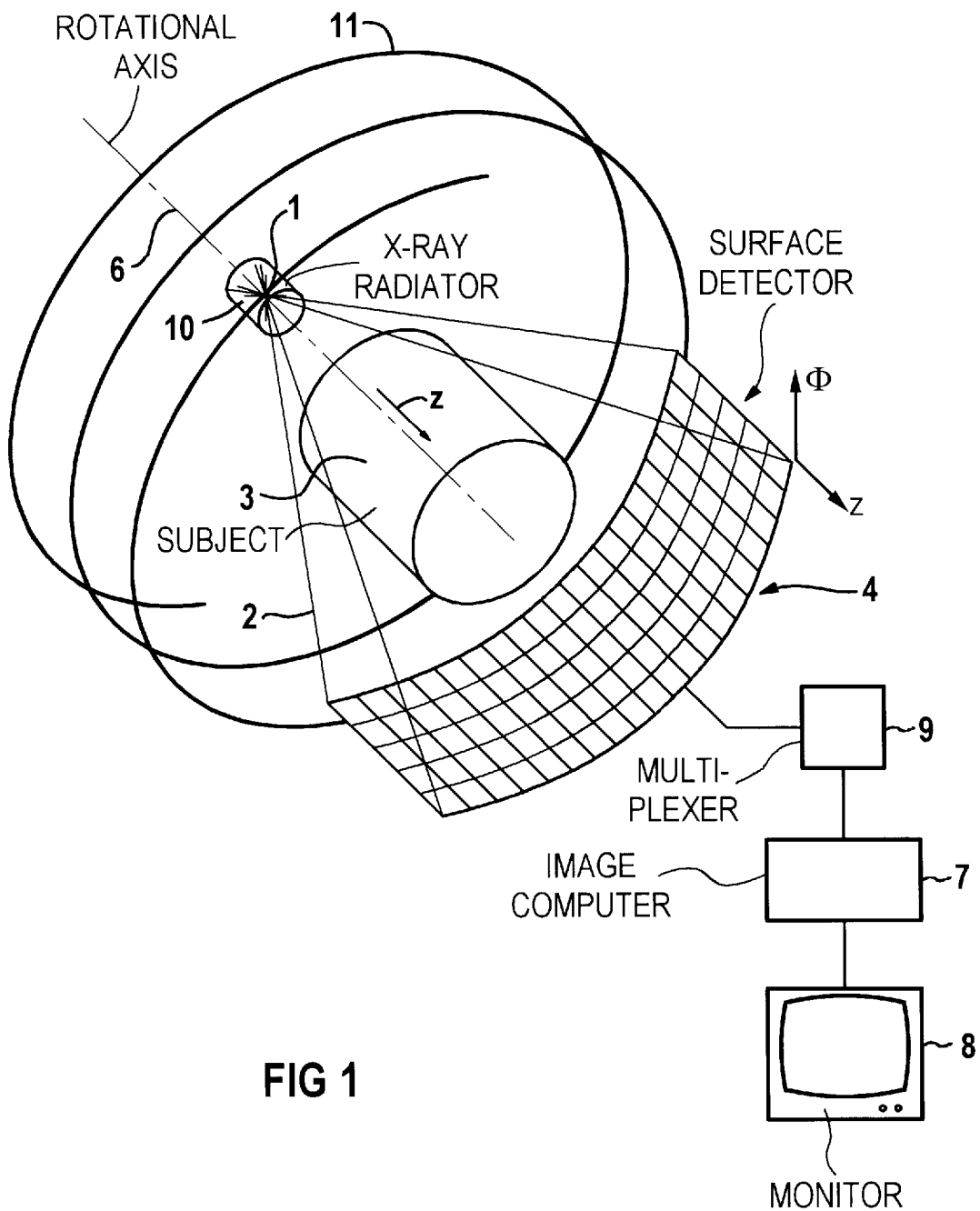
FIG. 1 is a schematic illustration of the basic components of a computed tomography with a surface detector constructed and operating in accordance with the principles of the present invention.

FIG. 1 shows the focus 1 of an X-ray radiator 10 from which a pyramidal X-ray beam 2 gated by a diaphragm (not shown) emanates, this X-ray beam 2 penetrating a subject 3 and striking a detector 4 that is composed of a number of parallel detector lines, each in turn formed of a number of detector elements. The measurement system, composed of the X-ray radiator 10 and the detector 4, is rotatable around a system axis 6, so that the subject 3 is transirradiated from various projections. A computer 7 calculates an image of the subject 3 from the detector signals that are thereby produced, this image being reproduced on a monitor 8. The acquisition of the detector signals ensues with a multiplexer 9.

Figure 2:
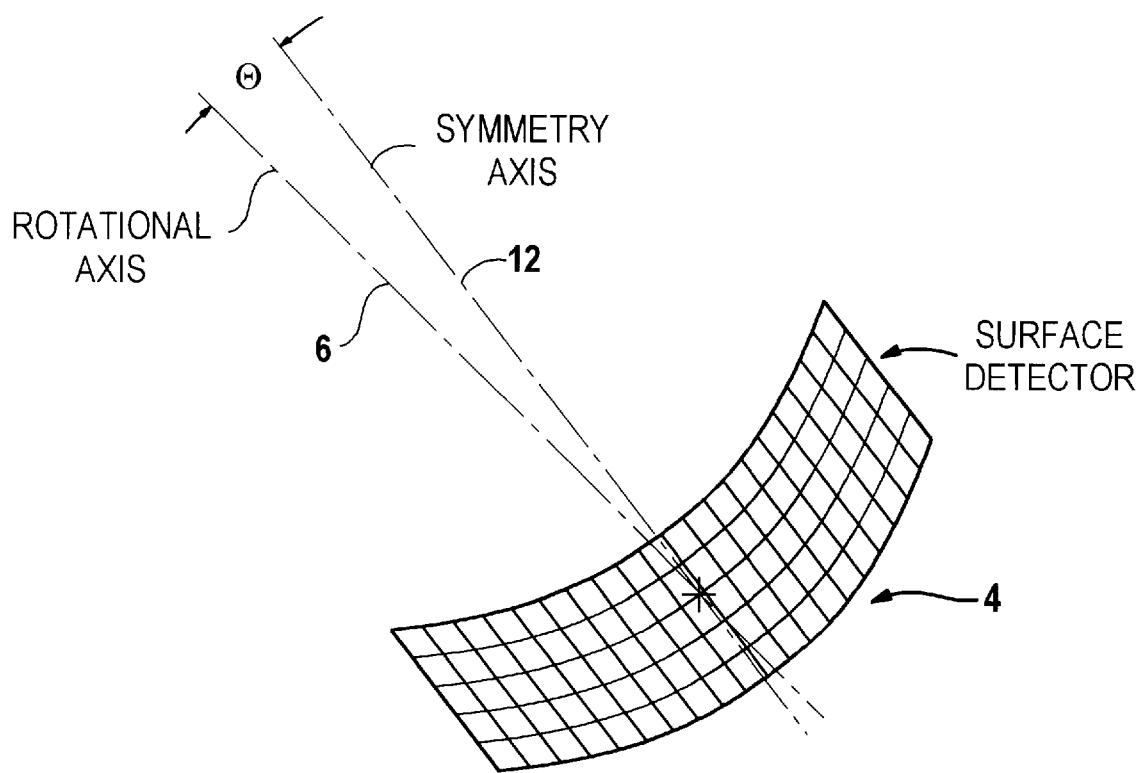
FIG. 2 is a schematic illustration of a detector arrangement for the computed tomography apparatus according to FIG. 1.

A volume scan is possible by causing the measurement system composed of the X-ray radiator 10 and the detector 4 to spirally scan the desired volume while rotating, as shown with the spiral 11 in FIG. 1. A relative motion between the measurement arrangement and the patient 3 thereby ensues in the direction of the system axis 6. For the spiral scan in accordance with the invention, the detector 4 is tilted relative to the system axis 6 according to FIG. 2. FIG. 2 shows the tilt angle $\ominus$ between the system axis 6 and the symmetry axis 12 of the detector 4. The detector 4 forms the part of a cylinder surface. For the illustrated inventive embodiment, the following relationship is valid for the angle $\ominus$:

$$\ominus = \tan^{-1}\left(\frac{1}{4\sqrt{2}} \cdot \frac{h}{a}\right)$$

In this equation h/a is the ratio of the slope of the spiral 11 to the radius. A specific detector can be utilized for different slopes of the inventive scan spiral by setting the angle $\ominus$ to a desired non-zero acute value. A conventional computed tomographic exposure can be prepared with the angle $\ominus$ made equal to 0, i.e. with the detector 4 set such that the axes 6 and 12 coincide.

Although the present invention has been described with reference to a specific embodiment, those of skill in the art will recognize that changes may be made thereto without departing from the scope and spirit of the invention as set forth in the appended claims.

We claim as our invention:

1. A computed tomography apparatus comprising:
   an X-ray radiator having a focus from which an X-ray beam emanates;
   a surface radiation detector composed of a plurality of parallel lines of detector elements, said detector elements being arranged symmetrically relative to a symmetry axis;
   means for conducting a spiral scan of an examination subject to obtain spiral scan data, by rotating said focus and said surface detector around a rotational axis around an examination subject, combined with relative longitudinal movement between said focus and said surface detector, and said examination subject; and means for mounting said surface detector, during said scan, with a non-zero acute angle between said symmetry axis and said rotational axis; and means for producing a tomogram of said examination subject from said spiral scan data.

2. A computed tomography apparatus as claimed in claim 1 wherein said means for mounting said surface detector comprises means for adjustably mounting said surface detector for adjusting said angle in a range which includes a value of 0.

3. A method for operating a computed tomography apparatus comprising:

providing an X-ray radiator having a focus and providing a surface detector composed of a plurality of parallel lines of detector elements, said detector elements being symmetrically arranged relative to a symmetry axis;

means for conducting a spiral scan of a volume of an examination subject to obtain spiral scan data, by rotating said focus and said surface detector around a rotational axis around said examination subject while producing relative longitudinal motion between said focus and said surface detector, and said examination subject;

during said scan, tilting said surface detector at a non-zero acute angle between said symmetry axis and said rotational axis; and producing a tomogram of said volume of said examination subject from said spiral scan data.

* * * * *